US00PP16173P3

(12) United States Plant Patent
Gruppe et al.

(10) Patent No.: US PP16,173 P3
(45) Date of Patent: Dec. 27, 2005

(54) ***PRUNUS* ROOTSTOCK NAMED 'GI 2091'**

(50) Latin Name: *Prunus* hybrid
Varietal Denomination: GI 2091

(75) Inventors: Werner Gruppe, Linden (DE); Hanna Schmidt, Marburg (DE)

(73) Assignee: Consortium Deutscher Baumschulen GmbH, Ellerbek (DE)

( * ) Notice: Subject to any disclaimer, the term of this patent is extended or adjusted under 35 U.S.C. 154(b) by 227 days.

(21) Appl. No.: 10/723,443

(22) Filed: Nov. 26, 2003

(65) Prior Publication Data

US 2005/0114958 P1 May 26, 2005

(51) Int. Cl.[7] ..... A01H 5/00
(52) U.S. Cl. ..... Plt./183
(58) Field of Search ..... Plt./180, 181, 183

*Primary Examiner*—Kent Bell
(74) *Attorney, Agent, or Firm*—Webb Ziesenheim Logsdon Orkin & Hanson, P.C.

(57) ABSTRACT

A new and distinct Interspecific *Prunus* hybrid plant used as a rootstock that exhibits dwarf-like productive growth.

2 Drawing Sheets

Botanical classification: Interspecific *Prunus* hybrid.
Varietal denomination: 'GI 2091'.

BACKGROUND OF THE INVENTION

The present invention comprises a new and distinct cultivar of Interspecific *Prunus* hybrid used as a rootstock known by the varietal name 'GI 2091'. The new variety was discovered in Giessen, Germany in 1969. The new variety is the result of a planned breeding program between *Prunus cerasus* 'Shattenmorelle' (unpatented female parent) and a *Prunus canescens* (male parent). The new variety differs from its parents in that it is a triploid genome. The purpose of the breeding program was to produce a series of dwarfing, precocious, productive rootstocks for sweet cherries. The new variety has been trial and field tested and has been found to retain its distinctive characteristics and remain true to type through successive propagations. 'GI 2091' IN COMPARISON TO CHERRY ROOTSTOCK 'GI 148/1' (U.S. Plant Pat. No. 8,954) AND CHERRY ROOTSTOCK 'GI 148/2' (U.S. Plant Pat. No. 9,622)

Leaf color: During main growth period, leaves of 'GI 2091' are somewhat brighter in colors than 148/1 and 148/2 (in autumn, there is no difference in color).

Habitus: In contrast to 148/1 and 148/2, which grow more upright, the habitus of 'GI 2091' is more weeping and it has more lateral branches.

Rooting system: 'GI 2091' has a finer root system and has fewer stronger roots than 148/1 and 148/2.

DESCRIPTION OF THE DRAWINGS

The accompanying photographic drawing illustrates the new cultivar, with the color being as nearly true as is possible with color illustrations of this type. The word Giessen in FIG. 1 is the location of discovery.

DESCRIPTION OF THE PLANT

Figure 1:
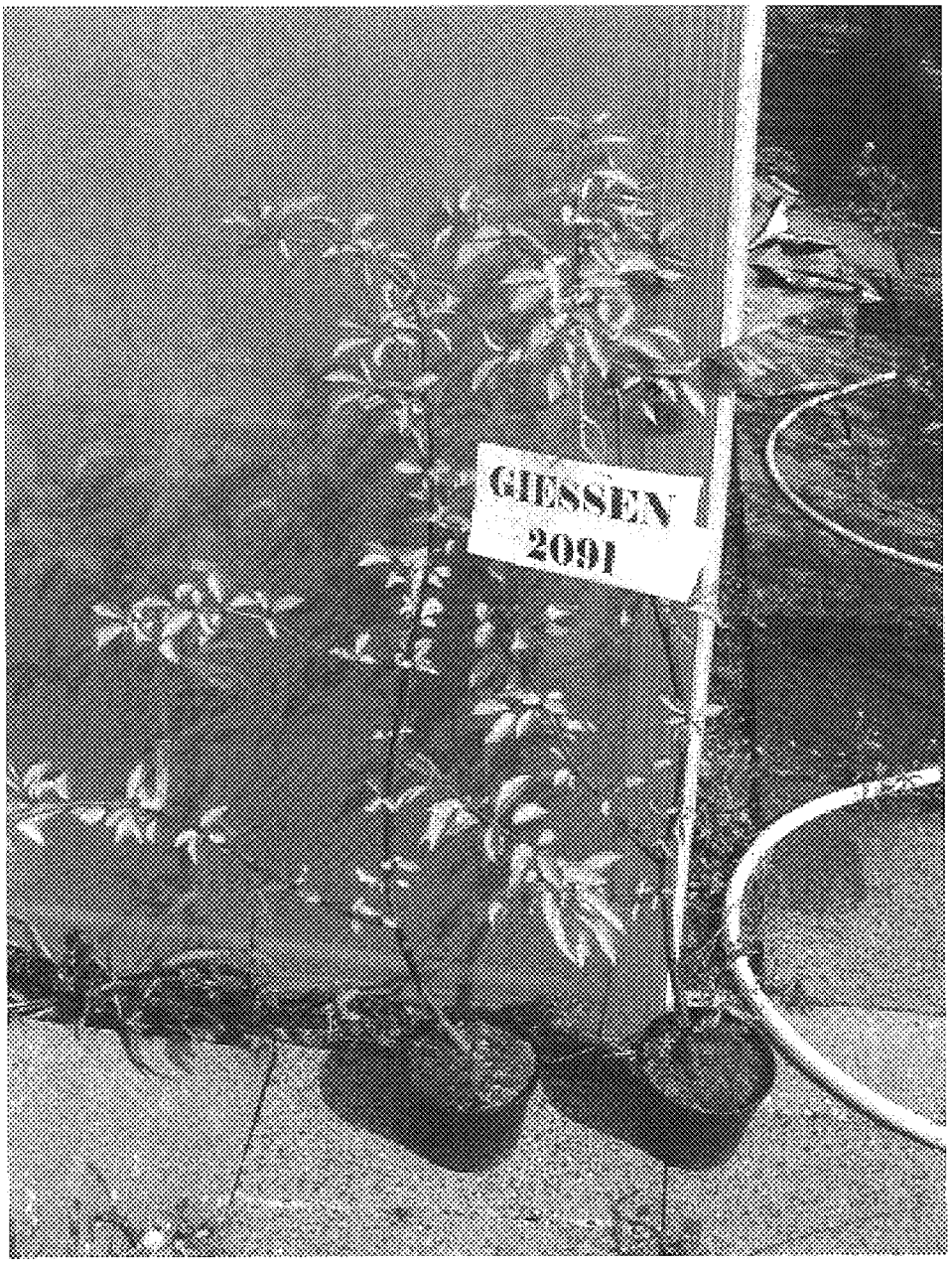
FIG. 1 illustrates two entire plants of the new variety.
Figure 2:
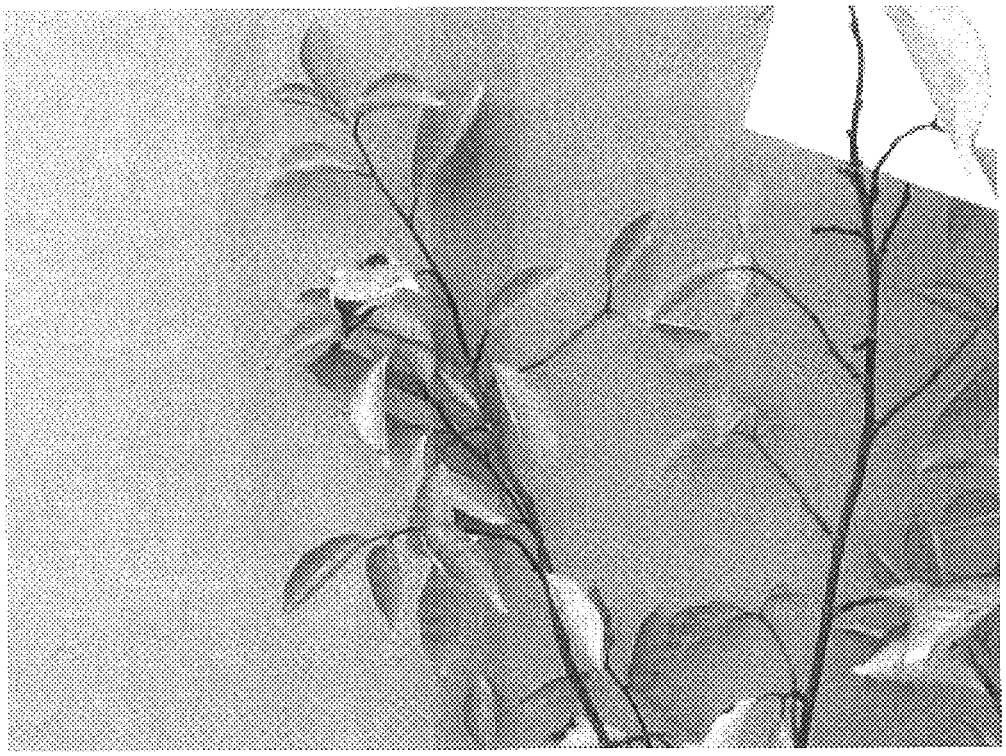
FIG. 2 is a close-up of the leaves and branches of the new variety.

The following detailed description sets forth the characteristics of the new cultivar. The data which defines these characteristics were collected by asexual reproductions carried by green cuttings under mist and in vitro conditions. The first and subsequent asexual reproductions occurred in approximately 1972 in Giessen, Germany. The plant was four years old when described. The color readings were taken in natural daylight. Color references are primarily to The R.H.S. Colour Chart of The Royal Horticultural Society of London.

PLANT

Use: Only as a rootstock.
Average tree height at top of foliage: 3 m.
Average tree diameter at the widest point: 3 m.
Form: Bushy; crown is more broad than high; flat branching.
Productivity: Early blooming and high blossom intensity.
Fruit bearing: Very rare.
USDA hardiness zone: 5.
Rooting habit: Freely branching and fibrous; highly dense.
Time to initiate roots: 3–4 weeks.
Disease and pest resistance: Tolerant to *Prunus* dwarf virus (PDV) and *Prunus* necrotic ringspot virus (PNRSV).
Trunk:
- *Diameter.*—12 mm at one year.
- *Height.*—150 cm.
- *Bark color.*—Surface: N186C. Flesh inside: 2C.
- *Lenticels.*—Color: 188D. Diameter: 1 mm. Arrangement: Irregular.

Branches:
- *Color.*—Surface: 199A. Flesh inside: 149D.
- *Internode length.*—Approximately 3 cm.
- *Branching angle at emergence.*—60–80°.
- *Diameter.*—Average diameter of a 1-year old branch is 4.5 mm.
- *Length.*—Average length of a 1-year old branch is 25 cm.
- *Pubescence.*—None.
- *Branch lenticels.*—Color: N170C. Diameter: 1 mm. Arrangement: Irregular.

Leaves:
- *Length.*—7.5 cm.
- *Width.*—4.2 cm.

*Shape.*—Lanceolate.
*Apex.*—Acuminate.
*Base.*—Rounded; elliptical.
*Color.*—Adaxial: 137A. Abaxial: 138A.
*Surface.*—Adaxial: Arched intercostal areas. Abaxial: Pilose.
*Margins.*—Serrated.
*Division.*—Leaves are entire, meaning not divided.
*Petiole.*—Length: 1.5 cm. Width: 1.5 mm. Color: 59B. Surface: Smooth.
*Leaf stipules.*—Presence: Two at the base of the petiole. Shape: Lanceolate. Length: 1.0 cm.
*Leaf pubescence.*—Slight.
*Venation pattern.*—Pinnate.
*Vein color.*—Adaxial: 138A. Abaxial: 145C.
*Leaf texture.*—Herbaceous.

Fruit:
*Shape.*—Round.
*Length.*—12.5 mm.
*Diameter.*—12.0 mm.
*Weight.*—0.9 g.
*Arrangement.*—Single.
*Skin color.*—46B.
*Flesh color.*—35B.
*Acidity.*—Light.
*Aroma.*—None.
*Taste.*—Bittersweet.

Flower:
*Arrangement.*—Single.
*Shape.*—Oblong.
*Bud.*—Shape: Acute apex with overlapping bud scales. Width: 3.0 mm. Length: 5.0 mm. Color: Closed: 178C. Before bursting: 179C. Time of bloom: April. Lastingness of entire plant bloom period: 20 days. Lastingness of an individual bloom on the plant: 10 days.
*Diameter.*—10–15 mm.
*Depth.*—10–15 mm.
*Bloom quantity.*—Very fertile; an enormous quantity of flowers.
*Petal.*—Number: Five. Length: 5 mm. Width: 7 mm. Texture: Velvet-like. Color: Upper surface: 69B. Lower surface: 69C. Margin: Rounded; entire.
*Flower color when fully opened.*—Upper surface: 69B. Lower surface: 69C.
*Peduncle.*—Length: 15–20 mm. Width: 1 mm. Surface: Smooth. Color: Upper surface: 59B. Lower surface: 59B.
*Sepal.*—Number: Five. Length: 1.7 mm. Diameter: 2.1 mm.
*Pedicel.*—Length: 27 mm. Diameter: 1 mm. Color: 20B.

Fragrance: Present.

Seed:
*Shape.*—Stone-like; oval.
*Length.*—8 mm.
*Diameter.*—5 mm.
*Color.*—23D.

Multiplication ability: Good via softwood cuttings.

Performance as a grafted rootstock:
*Root sprouts.*—No suckers observed.
*Anchorage.*—Needs support.
*Compatibility.*—Good virus-free budding material.
*Vigor.*—Strong growth reduction.

REPRODUCTIVE ORGANS

Stamens:
*Number.*—Five.
*Length.*—10–15 mm.
*Color.*—Yellow-green.

Anthers:
*Shape.*—Rounded.
*Color.*—Yellow-brown.
*Length.*—1.0 mm.
*Width.*—0.5–1.0 mm.
*Amount of pollen.*—Average.
*Color of pollen.*—Yellow.
*Stigma color.*—Green.

Pistils:
*Number.*—One.
*Length.*—2.0–3.0 mm.

Style:
*Color.*—Green.
*Form.*—Rounded.
*Length.*—2.0 mm.
*Width.*—1.5–2.0 mm.

Ovaries:
*Length.*—3.0 mm.
*Width.*—2.0 mm.
*Color.*—Green.
*Position.*—Protruding.

ADDITIONAL INFORMATION

Enzyme polymorphism (horizontal starch gel electrophoresis of leaf tissue of 8 loci) of 'GI 2091':

| | |
|---|---|
| Aconitase-2 | 24 |
| Alcoholdehydrogenase-1 | 1 |
| Isocitratdehydrogenase-2 | 112 |
| Leucinaminopeptidase-1 | 23 |
| 6-Phosphogluconat-Dehydrogenase-1 | 11 H |
| 6-Phosphogluconat-Dehydrogenase-2 | 122 |
| Phosphoglucose-Isomerase-2 | 24 |
| Phosphoglucomutase-2 | 25 |

I claim:

1. A new and distinct variety of Interspecific *Prunus* hybrid substantially as shown and described.

* * * * *